US010620702B2

(12) United States Patent
Imajo et al.

(10) Patent No.: US 10,620,702 B2
(45) Date of Patent: Apr. 14, 2020

(54) INTERNAL DEVICE OF BRAIN-MACHINE INTERFACE SYSTEM INCLUDING NOISE REDUCTION TECHNIQUE, AND METHOD OF CONTROLLING THE INTERNAL DEVICE

(71) Applicants: NIHON KOHDEN CORPORATION, Shinjuku-ku, Tokyo (JP); OSAKA UNIVERSITY, Suita-shi, Osaka (JP); NATIONAL INSTITUTE OF INFORMATION AND COMMUNICATIONS TECHNOLOGY, Koganei-shi, Tokyo (JP)

(72) Inventors: Kaoru Imajo, Tokyo (JP); Katsuyoshi Suzuki, Tokyo (JP); Masayuki Hirata, Suita (JP); Seiji Kameda, Suita (JP); Takafumi Suzuki, Koganei (JP); Hiroshi Ando, Koganei (JP)

(73) Assignees: NIHON KOHDEN CORPORATION, Tokyo (JP); OSAKA UNIVERSITY, Osaka (JP); NATIONAL INSTITUTE OF INFORMATION AND COMMUNICATIONS TECHNOLOGY, Tokyo (JP)

( * ) Notice: Subject to any disclaimer, the term of this patent is extended or adjusted under 35 U.S.C. 154(b) by 251 days.

(21) Appl. No.: 15/800,613

(22) Filed: Nov. 1, 2017

(65) Prior Publication Data
US 2018/0120937 A1    May 3, 2018

(30) Foreign Application Priority Data
Nov. 2, 2016   (JP) ................................. 2016-215375

(51) Int. Cl.
*A61B 5/04* (2006.01)
*G06F 3/01* (2006.01)
(Continued)

(52) U.S. Cl.
CPC ............ *G06F 3/015* (2013.01); *A61B 5/0006* (2013.01); *A61B 5/04004* (2013.01);
(Continued)

(58) Field of Classification Search
CPC ........... A61B 5/00; A61B 5/04; A61B 5/0478; A61B 5/0006; A61B 5/04012;
(Continued)

(56) References Cited

U.S. PATENT DOCUMENTS 2,920,281 A    1/1960   Appert et al.
4,300,101 A *  11/1981  Shvartsman ......... H03G 3/3005
                                                     330/136
(Continued)

OTHER PUBLICATIONS

Communication dated Mar. 5, 2018, issued by the European Patent Office in counterpart European application No. 17199656.4.

*Primary Examiner* — Eric J Messersmith
(74) *Attorney, Agent, or Firm* — Sughrue Mion, PLLC

(57) ABSTRACT

An internal device of a brain-machine interface system includes: an electrode group including N electrodes, N being 2 or more; an amplification element group including N amplification elements; a communicator communicating with an external device; and a controller selectively executing one of: a normal operation mode in which electroencephalogram signals acquired through the N electrodes are supplied to the amplification element group in a manner that each of the N electrodes corresponds to a respective one of the N amplification elements, and N amplified electroencephalogram signals are transmitted; and a noise-reduction operation mode in which an electroencephalogram signal acquired through an M electrode of the electrode group is (Continued)

supplied to the amplification element group in a manner that each M electrode corresponds to respective plural ones of the amplification elements, and an M amplified electroencephalogram signal is transmitted, M being smaller than N.

10 Claims, 7 Drawing Sheets

(51) Int. Cl.
    *A61B 5/0476*     (2006.01)
    *A61B 5/00*     (2006.01)
    *A61B 5/0478*     (2006.01)

(52) U.S. Cl.
    CPC ........ *A61B 5/04012* (2013.01); *A61B 5/0476* (2013.01); *A61B 5/0478* (2013.01); *A61B 5/6868* (2013.01); *A61B 5/7203* (2013.01); *A61B 2562/0209* (2013.01)

(58) Field of Classification Search
    CPC . A61B 5/6868; A61B 5/7203; A61B 5/04004; A61B 5/0476; A61B 2562/0209; G06F 3/015
    See application file for complete search history.

(56) References Cited

U.S. PATENT DOCUMENTS

| | | |
|---|---|---|
| 6,463,322 B1 | 10/2002 | Lutz et al. |
| 2006/0049957 A1 | 3/2006 | Surgenor et al. |
| 2008/0021514 A1 | 1/2008 | Pless |
| 2016/0278713 A1 | 9/2016 | Shoaran et al. |
| 2017/0332973 A1* | 11/2017 | Durand ................ A61B 5/7203 |

* cited by examiner

INTERNAL DEVICE OF BRAIN-MACHINE INTERFACE SYSTEM INCLUDING NOISE REDUCTION TECHNIQUE, AND METHOD OF CONTROLLING THE INTERNAL DEVICE

CROSS-REFERENCE TO RELATED APPLICATION(S)

This application is based upon and claims the benefit of priority from prior Japanese patent application No. 2016-215375, filed on Nov. 2, 2016, the entire contents of which are incorporated herein by reference.

BACKGROUND

The presently disclosed subject matter relates to a brain-machine interface (BMI) system including: an internal device which is to be implanted in the living body; and an external device which is to be placed outside the living body, particularly to the internal device and a method of controlling the internal device.

An internal device acquires brain waves functioning as a signal source to detect the brain activity, and transmits a signal which corresponds to the brain activity, or that which is obtained by processing the signal, to an external device. The external device operates in accordance with the signal received from the internal device. The internal device disclosed in US 2006/0049957 A1 includes a plurality of electrodes which are to be implanted in the living body to detect brain waves.

An internal device such as described above is implanted in the brain of a patient with amyotrophic lateral sclerosis (ALS) or the like, and communication with the patient is supported. In ALS, in the case of strong degeneration of upper motor neurons, however, brain waves gradually diminish. In order to adequately acquire diminished electroencephalogram signals, it is necessary to design the low-noise performance of a group of signal amplification elements which are mounted on the internal device, while anticipating the levels of the diminished electroencephalogram signals. When such a design is employed, however, the size increase of the internal device due to the scale enlargement of an amplification circuit, and heat generation due to the increase of power consumption are inevitable. Therefore, the design is not adequate for an implantable type internal device.

SUMMARY

The presently disclosed subject matter may provide an internal device of a brain-machine interface system and a method of controlling the internal device capable of performing the BMI control for a long period of time, even with respect to a patient in whom the intensity of brain waves is reduced with progression of disease.

The internal device of a brain-machine interface system, adapted to be implanted in a living body, may include: an electrode group which includes N electrodes acquiring electroencephalogram signals of the living body, wherein N is 2 or more; an amplification element group which includes N amplification elements; a communicator which is configured to wirelessly communicate with an external device; and a controller which is configured to control an electrical connection between the electrode group and the amplification element group, and which is configured to control the communicator, the controller which is configured to selectively execute one of: a normal operation mode in which electroencephalogram signals of the living body that are acquired through the N electrodes of the electrode group are supplied to the amplification element group in a manner that each of the N electrodes corresponds to a respective one of the N amplification elements, and the communicator is caused to wirelessly transmit N amplified electroencephalogram signals; and a noise-reduction operation mode in which an electroencephalogram signal of the living body that is acquired through an M electrode of the electrode group is supplied to the amplification element group in a manner that each M electrode corresponds to respective plural ones of the amplification elements, and the communicator is caused to wirelessly transmit an M amplified electroencephalogram signal, wherein M is smaller than N.

DETAILED DESCRIPTION OF EXEMPLARY EMBODIMENTS

Hereinafter, an embodiment will be described in detail with reference to the accompanying drawings.

Figure 1:
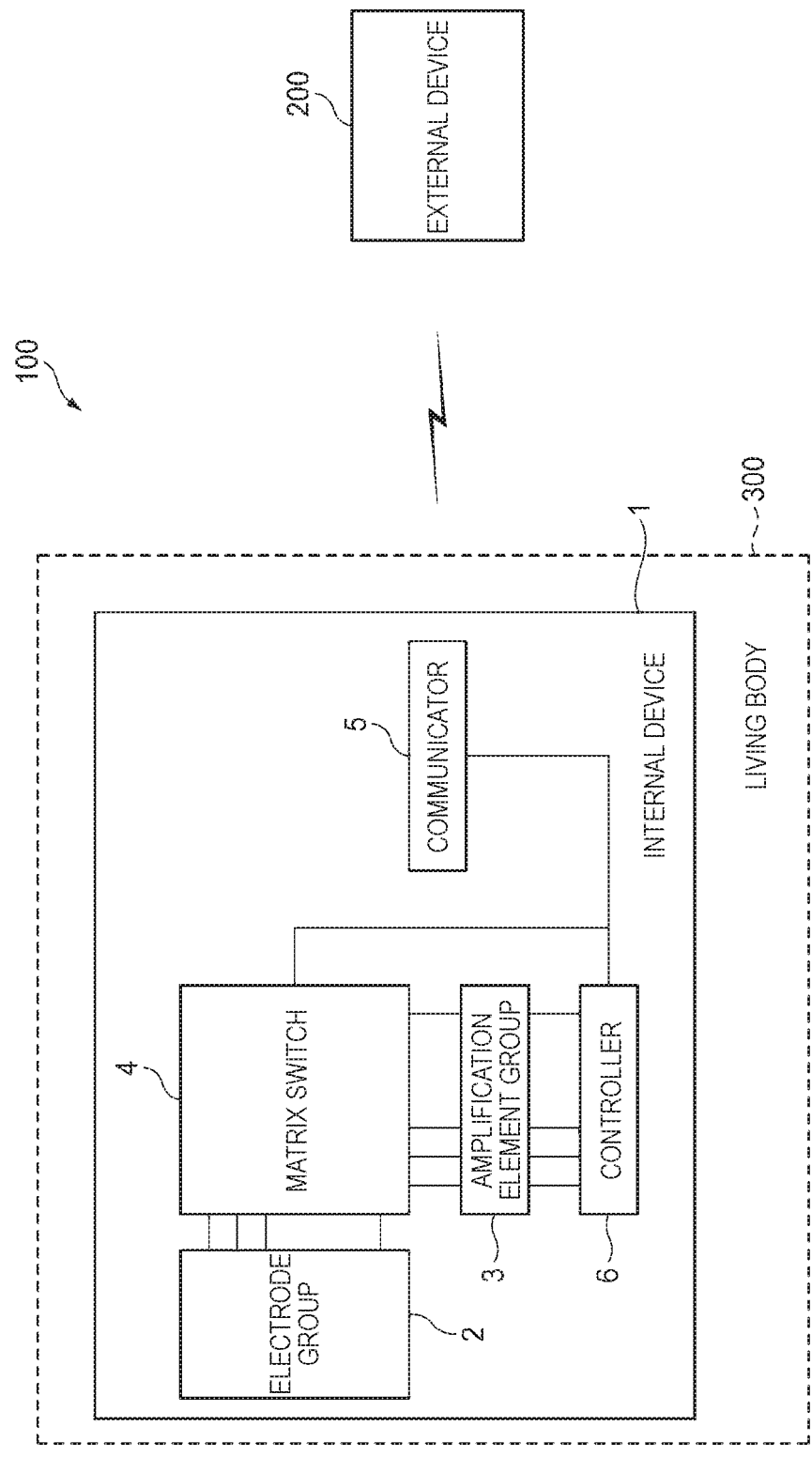
FIG. 1 is a block diagram showing the functional configuration of a BMI system which is an embodiment.

FIG. 1 shows the functional configuration of a BMI system 100 of an embodiment. The BMI system 100 includes an internal device 1 and an external device 200. The internal device 1 is configured so as to be used while being implanted in the living body 300 (specifically, the head). The external device 200 is configured so as to be used while being placed outside the living body 300.

The internal device 1 includes an electrode group 2 including N electrodes. In the following description, N is an integer of 2 or more. Each of the electrodes of the electrode group 2 is configured so as to be attached to a predetermined place of the brain of the living body 300, and acquire an electroencephalogram signal in the place.

The internal device 1 further includes: an amplification element group 3 including N amplification elements; and a matrix switch 4. The amplification element group 3 is electrically connected to the electrode group 2 through the matrix switch 4. Each of the amplification elements of the amplification element group 3 is configured so as to amplify an input signal, and output the amplified signal.

The internal device 1 further includes a communicator 5. The communicator 5 is electrically connected to output terminals of the amplification element group 3. The communicator 5 is configured so as to be able to wirelessly communicate with the external device 200.

The internal device 1 further includes a controller 6. The controller 6 is configured so as to operate the matrix switch 4 to control the electrical connection state between the electrode group 2 and the amplification element group 3.

The controller 6 is also configured so as to be able to control the operation of the communicator 5.

Figure 2:
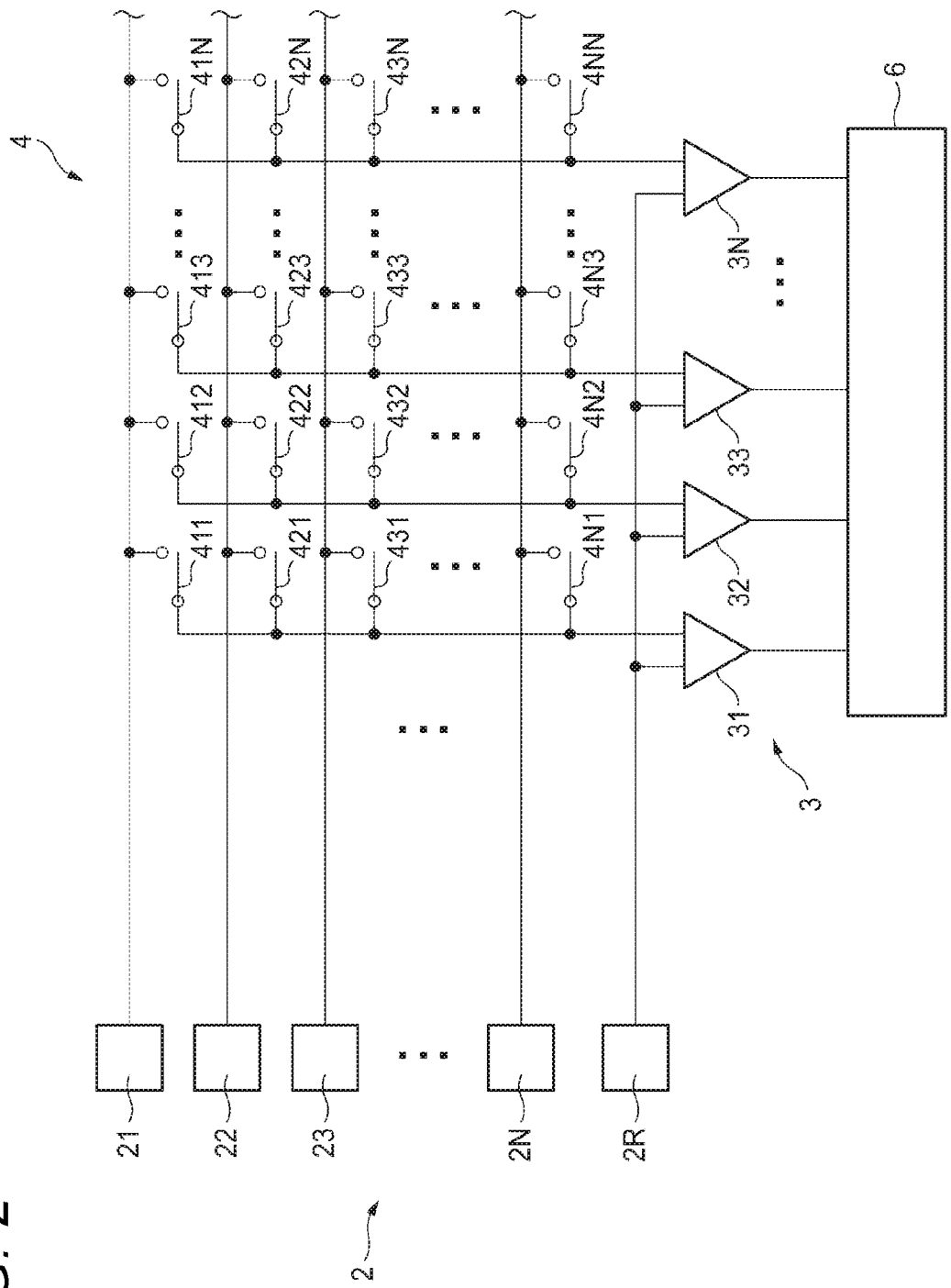
FIG. 2 is a circuit diagram showing a part of an internal device of the BMI system.

FIG. 2 specifically shows the circuit configuration of a part of the internal device 1. The electrode group 2 includes N electrodes 21, 22, 23, . . . , 2N. The amplification element group 3 includes N amplification elements 31, 32, 33, . . . , 3N.

The matrix switch 4 includes an N×N number of switch elements. Each of the switch elements is electrically connected to the controller 6 through a signal line which is not shown. Therefore, the controller 6 can control the opening/closing operation of each of the switch elements.

The matrix switch includes switch elements 411, 412, 413, . . . , 41N. The input ends of the switch elements 411, 412, 413, . . . , 41N are electrically connected to the electrode 21.

The matrix switch further includes switch elements 421, 422, 423, . . . , 42N. The input ends of the switch elements 421, 422, 423, . . . , 42N are electrically connected to the electrode 22.

The matrix switch further includes switch elements 431, 432, 433, . . . , 43N. The input ends of the switch elements 431, 432, 433, . . . , 43N are electrically connected to the electrode 23.

The matrix switch further includes switch elements 4N1, 4N2, 4N3, . . . , 4NN. The input ends of the switch elements 4N1, 4N2, 4N3, . . . , 4NN are electrically connected to the electrode 2N.

The output ends of the switch elements 411, 421, 431, . . . , 4N1 are electrically output to the amplification element 31. When the switch element 4N1 is closed, for example, the electroencephalogram signal which is acquired by the electrode 2N is supplied to the amplification element 31.

The output ends of the switch elements 412, 422, 432, . . . , 4N2 are electrically output to the amplification element 32. When the switch element 432 is closed, for example, the electroencephalogram signal which is acquired by the electrode 23 is supplied to the amplification element 32.

The output ends of the switch elements 413, 423, 433, . . . , 4N3 are electrically output to the amplification element 33. When the switch element 423 is closed, for example, the electroencephalogram signal which is acquired by the electrode 22 is supplied to the amplification element 33.

The output ends of the switch elements 41N, 42N, 43N, . . . , 4NN are electrically output to the amplification element 3N. When the switch element 41N is closed, for example, the electroencephalogram signal which is acquired by the electrode 21 is supplied to the amplification element 3N.

The electrode group 2 further includes an electrode 2R. The electroencephalogram signal which is acquired through the electrode 2R is supplied as a reference potential signal to the amplification elements 31, 32, 33, . . . , 3N, respectively. Namely, the electrode 2R is used as the reference potential supply source.

Each of the amplification elements 31, 32, 33, . . . , 3N is configured so as to amplify the difference between the input electroencephalogram signal and the reference potential signal, by a predetermined amplification factor, and output the amplified signal. The amplified electroencephalogram signals which are output respectively from the amplification elements 31, 32, 33, . . . , 3N are supplied to the controller 6.

Figure 3:
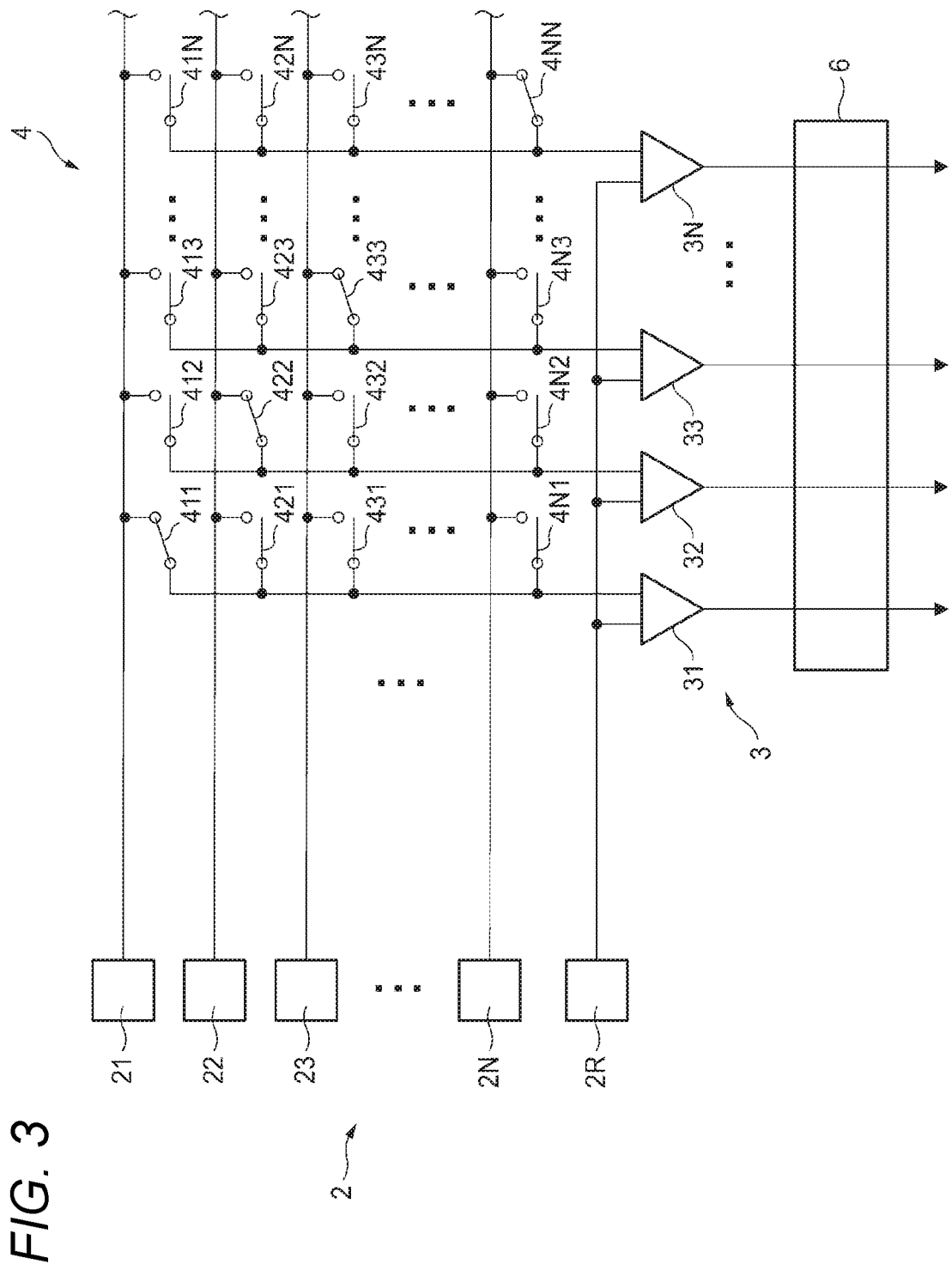
FIG. 3 is a circuit diagram illustrating the operation of the internal device.
Figure 4:
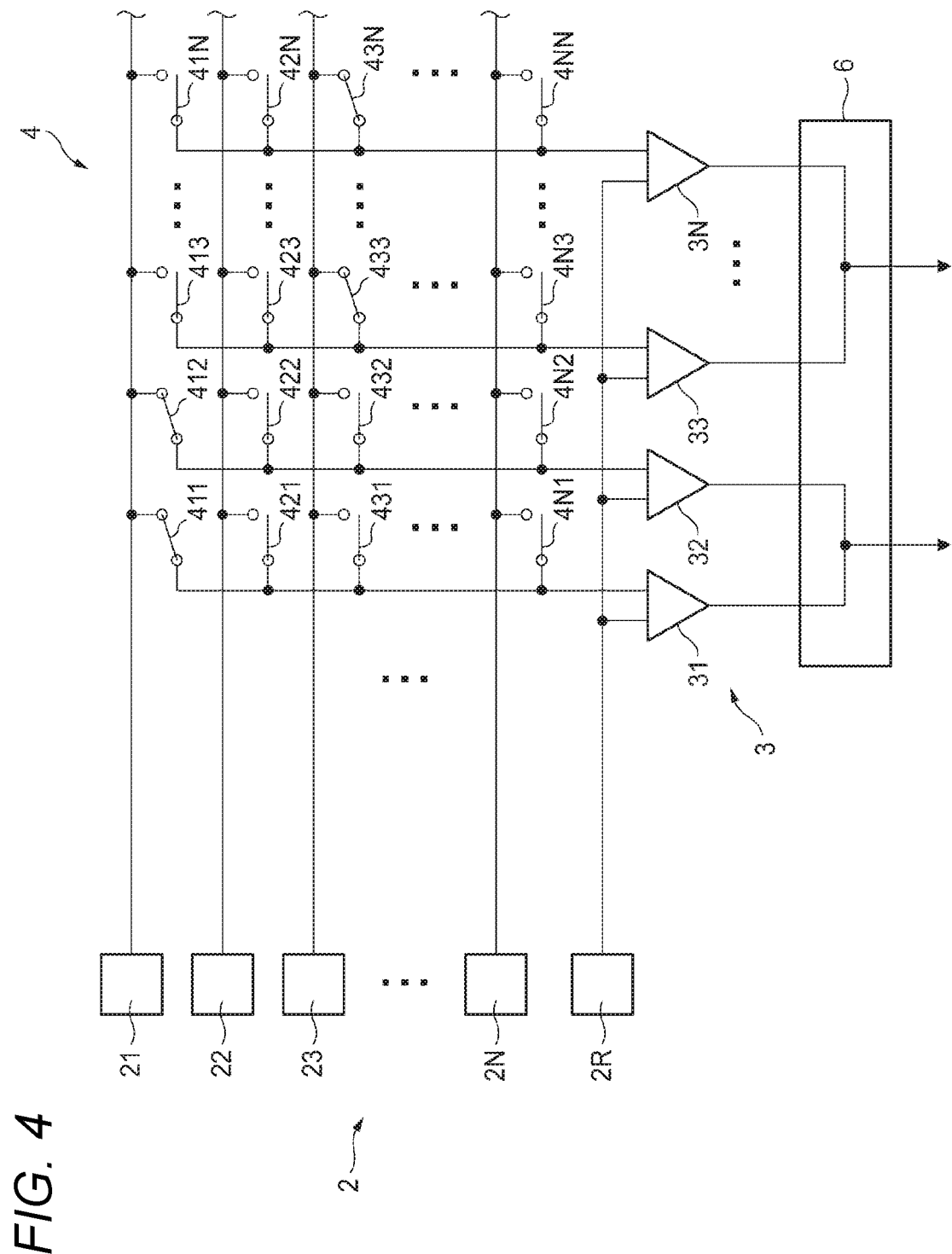
FIG. 4 is a circuit diagram illustrating the operation of the internal device.

The controller 6 is configured so as to selectively execute one of a normal operation mode and a noise-reduction operation mode. FIG. 3 shows a configuration example of the matrix switch 4 during execution of the normal operation mode, and FIG. 4 shows a configuration example of the matrix switch 4 during execution of the noise-reduction operation mode.

When the normal operation mode is executed, the controller 6 causes the electroencephalogram signals of the living body 300 which are acquired through the N electrodes of the electrode group 2, to the N amplification elements of the amplification element group 3, in such a manner that each of the electrodes corresponds to a respective one of the amplification elements.

As shown in FIG. 3, for example, the controller 6 controls the matrix switch 4 so that the switch elements 411, 422, 433, . . . , 4NN are closed. Therefore, the electroencephalogram signal acquired through the electrode 21 is supplied to the amplification element 31. Similarly, the electroencephalogram signal acquired through the electrode 22 is supplied to the amplification element 32, that acquired through the electrode 23 is supplied to the amplification element 33, and that acquired through the electrode 2N is supplied to the amplification element 3N.

As a result, the N amplified electroencephalogram signals which are output from the amplification elements 31, 32, 33, . . . , 3N are supplied to the controller 6. The controller 6 relays directly the N amplified electroencephalogram signals which are input thereto, to the communicator 5. Thereafter, the controller 6 causes the communicator 5 to wirelessly transmit the N amplified electroencephalogram signals at a predetermined timing. The amplified electroencephalogram signals which are wirelessly transmitted are received by the external device 200. The external device 200 operates in accordance with the received and amplified electroencephalogram signals.

The external device 200 may be identical with or different from a device which receives the signals transmitted from the internal device 1, and which executes an operation based on the signals. For example, the external device 200 may be a device which receives the signals transmitted from the internal device 1, and which transmits a control signal that causes another external device to execute the operation based on the transmitted signals.

When the noise-reduction operation mode is executed, the controller 6 causes the electroencephalogram signals of the living body 300 which are acquired through an M number of electrodes (M is smaller than N) of the electrode group 2, to be supplied to the amplification element group 3 in such a manner that each electrode corresponds to respective plural ones of the amplification elements.

As shown in FIG. 4, for example, the controller 6 controls the matrix switch 4 so that the switch elements 411, 412, 433, . . . , 43N are closed. Therefore, the electroencephalogram signal acquired through the electrode 21 is supplied in parallel to the amplification elements 31, 32. Similarly, the electroencephalogram signal acquired through the electrode 23 is supplied in parallel to the amplification element group including the amplification elements 33, 3N. In this example, namely, M is 2.

Next, the controller 6 performs a process of arithmetically averaging the amplified electroencephalogram signals which are output from the plurality of amplification elements that correspond to each of the M electrodes. In this example, the amplified electroencephalogram signals which are output from the amplification elements 31, 32 that correspond to the electrode 21 are arithmetically averaged. Similarly, the amplified electroencephalogram signals which are output from the amplification elements 33, 3N that correspond to the electrode 23 are arithmetically averaged. As a result, the controller 6 acquires M (in the example, M is 2) arithmetically averaged and amplified electroencephalogram signals.

It is known that, when a signal with noises is supplied to n amplification elements, and the n amplified signal which are output from the n amplification elements are arithmetically averaged, the noise level of the obtained signal is reduced to $1/\sqrt{n}$ as compared to that of the signal which has not been arithmetically averaged. In this example, therefore, the noise level can be reduced to $1/\sqrt{2}$ by arithmetically averaging the amplified electroencephalogram signals which are output from the amplification elements 31, 32. In the case where m amplification elements are included in the amplification element group that includes the amplification elements 33, 3N, similarly, the noise level can be reduced to $1/\sqrt{m}$ by arithmetically averaging amplified electroencephalogram signals output from the amplification element group.

The controller 6 relays the M amplified electroencephalogram signals in which the noise level is reduced, to the communicator 5. Thereafter, the controller 6 causes the communicator 5 to wirelessly transmit the M amplified electroencephalogram signals at a predetermined timing. The amplified electroencephalogram signals which are wirelessly transmitted are received by the external device 200. The external device 200 operates in accordance with the received and amplified electroencephalogram signals.

Next, a method of operating the thus configured internal device 1 will be described. It is assumed that the living body 300 is a patient in whom brain waves diminish with progression of disease. An example of disease is ALS. The internal device 1 is implanted in the head of the patient in a stage where communication with the patient can be well performed.

The controller 6 first executes the normal operation mode. In the normal operation mode, electroencephalogram signals of the patient are acquired by using the electrode group 2 including as many (N) electrodes as possible, and therefore also the number of channels for the amplified electroencephalogram signals which are supplied to the external device 200 through the communicator 5 is maximum. Consequently, a rapid BMI control having a high degree of freedom can be performed.

With progression of disease, the brain waves of the patient diminish, and the SN ratios of the acquired electroencephalogram signals are lowered. When it is determined that it is difficult to perform a significant BMI control based on the brain waves which are acquired in the normal operation mode, the controller 6 executes the noise-reduction operation mode.

Specifically, M electrodes which are to continue to acquire electroencephalogram signals are selected from the N electrodes of the electrode group 2. Through observation of the BMI control performed in the normal operation mode, the M electrodes are selected as an electrode group with higher priority to perform a significant BMI control. The selected M electrodes may be varied depending on the patient. A signal designating the selected M electrodes is wirelessly transmitted from the external device 200, and then received by the communicator 5. Based on the signal received by the communicator 5, the controller 6 operates the matrix switch 4.

Each of M electroencephalogram signals in which the SN ratio is lowered is supplied to a plurality of amplification elements. The amplified electroencephalogram signals which are output from the plurality of amplification elements are arithmetically averaged. As a result, M amplified electroencephalogram signals in which the noise level is lowered as compared with the case of the normal operation mode are obtained. The number of used electrodes, i.e., the channel number is reduced, and therefore it is unavoidable that the degree of freedom of the BMI control is lowered. In brain waves of the patient, however, small changes, which, in the related art, are buried in noise can be distinguished. Even with respect to a patient in whom the intensity of brain waves is reduced with progression of disease, therefore, the possibility of the BMI control can be provided for a long period of time.

In the embodiment, the function of the controller 6 is realized from software executed by a cooperation of a processor and memory which are communicably connected to each other. Examples of the processor are a CPU and an MPU. Examples of the memory are a RAM and a ROM. However, the function of the controller 6 may be realized by hardware such as an ASIC or an FPGA, or a combination of hardware and software.

The above-described embodiment is a mere example for facilitating understanding of the presently disclosed subject matter. The configuration of the embodiment may be adequately changed or improved without departing the spirit of the presently disclosed subject matter. It is obvious that equivalents are included within the technical scope of the presently disclosed subject matter.

Figure 5:
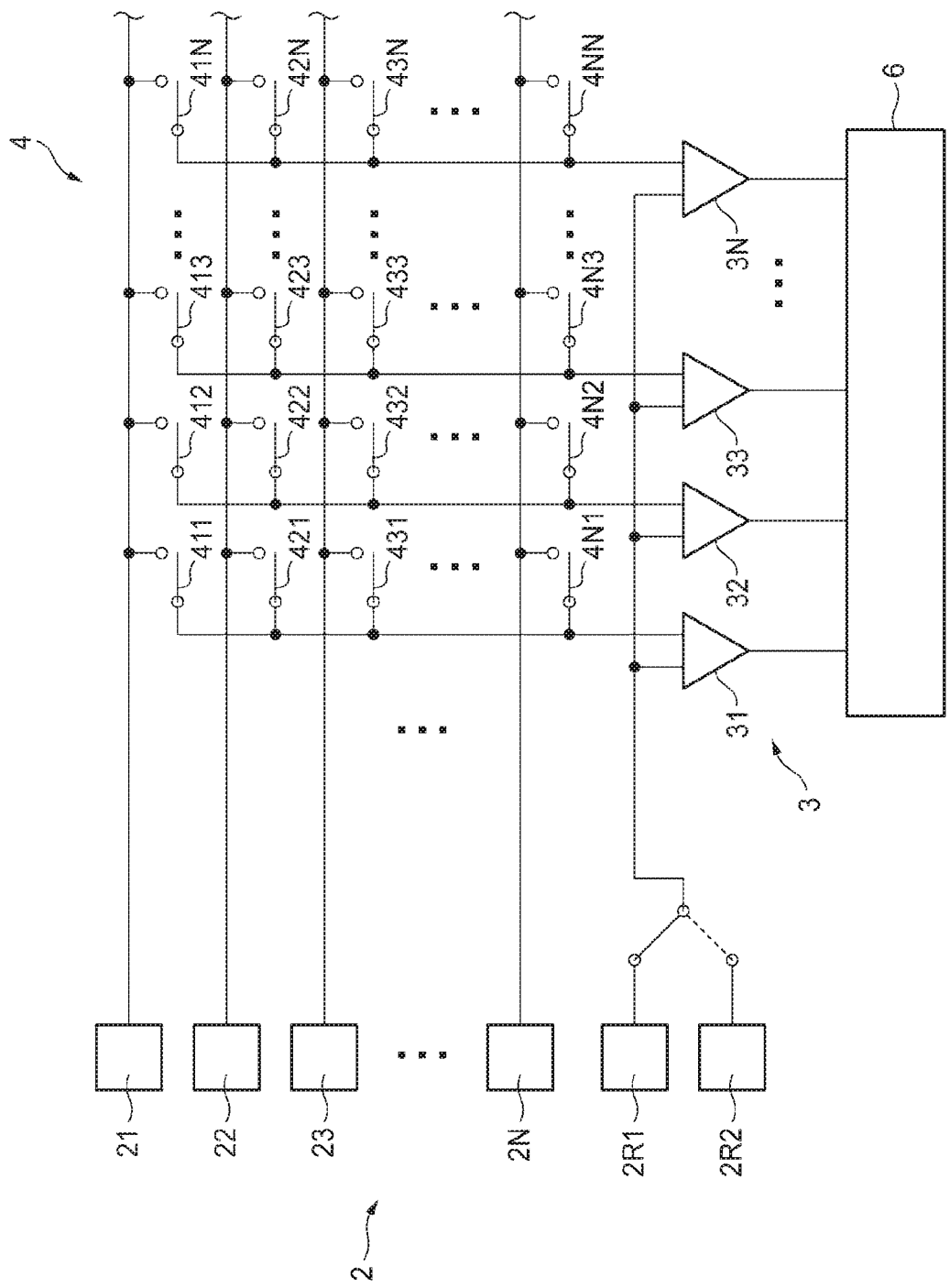
FIG. 5 is a circuit diagram showing a modification of the internal device.

In the above-described embodiment, the electroencephalogram signal acquired by the electrode 2R is supplied as the reference potential signal to each of the amplification elements of the amplification element group 3. Alternatively, a configuration may be employed in which, as shown in FIG. 5, one of two electrodes 2R1, 2R2 (an example of the plurality of reference potential supply sources) is electrically connected to the amplification element group 3 in a switchable manner. The number of switchable electrodes may be 3 or more.

The internal device 1 is used while being implanted in the living body 300, and therefore cannot be easily taken out from the body after the operation is started. According to the configuration, even when any failure occurs in the electrode 2R1 which is originally used as the reference potential supply source, the reference potential supply source can be switched to the other electrode 2R2, so that the amplification element group 3 can continue to operate. Therefore, the number of opportunities of exchanging the internal device 1 which impose a burden on the patient can be reduced, and the possibility of the BMI control can be provided for a long period of time.

Figure 6:
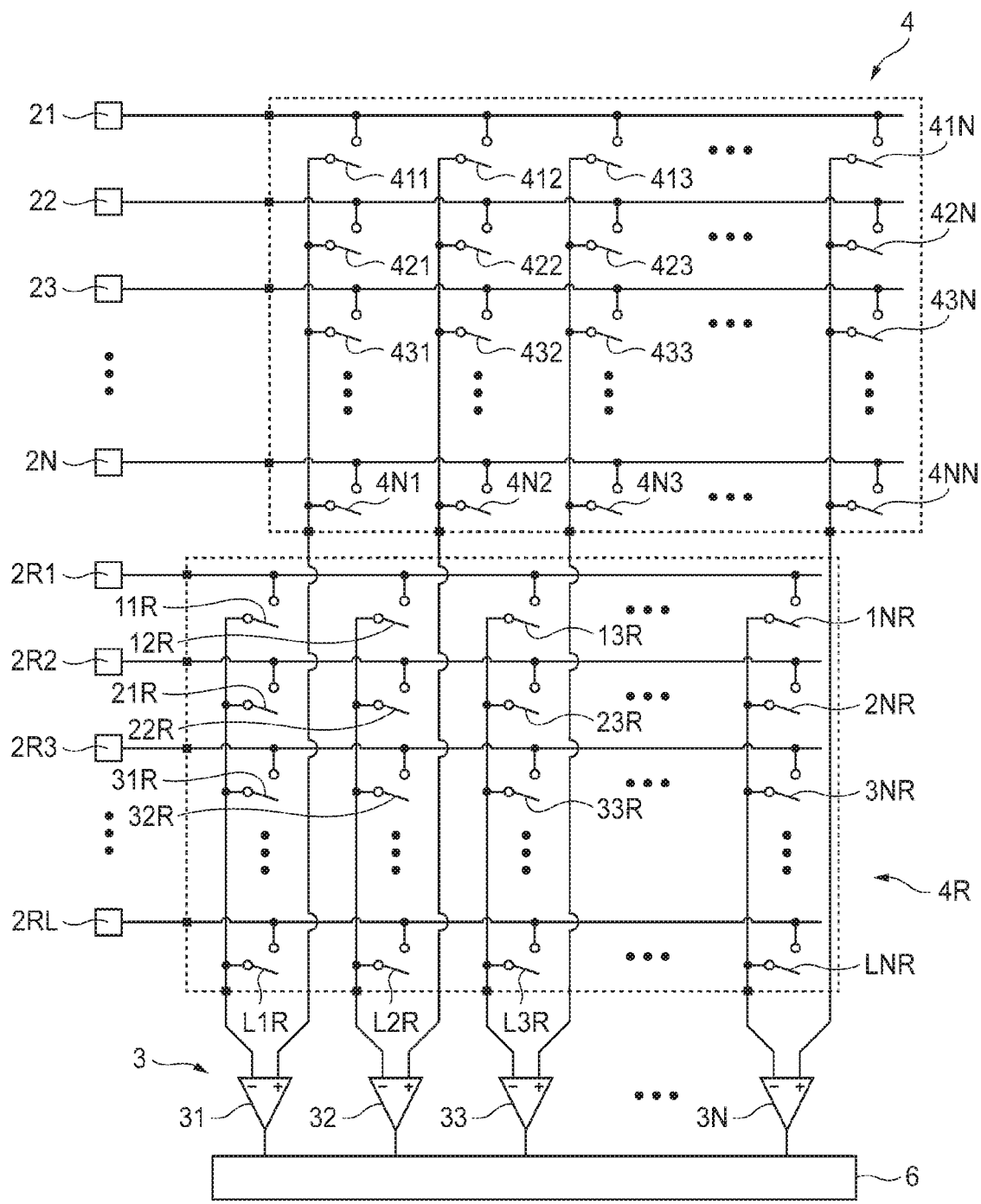
FIG. 6 is a circuit diagram showing another modification of the internal device.

A configuration may be employed that, as shown in FIG. 6, includes a matrix switch 4R in which the above-described function of switching between the electrodes 2R1, 2R2 is more generalized. The matrix switch 4R includes L×N switch elements (11R, 12R, . . . , LNR). Here, L is an integer of N or less. The electrode group 2 includes L electrodes 2R1, 2R2, 2R3, . . . , 2RL.

When all switch elements in which the input end is connected to one of the electrodes 2R1 to 2RL (for example, the switch elements 31R to 3NR connected to the electrode 2R3) are closed, the potential which is supplied through the electrode 2R3 is supplied as the reference potential or a differential input to the amplification elements 31 to 3N.

When switch elements which are arbitrarily selected from the switch elements 411 to 4NN included in the matrix switch 4, and the switch elements 11R to LNR included in the matrix switch 4R are closed, alternatively, the electroencephalogram signal acquired by one of the electrodes 21 to 2N, and the reference potential or differential input acquired by one of the electrodes 2R1 to 2RL can be supplied to any one of the amplification elements 31 to 3N.

A switch signal is wirelessly transmitted from the external device 200, and then received by the communicator 5. Based on the received signal, the switching of the reference potential supply sources can be performed by the controller 6. Alternatively, a configuration may be employed in which the controller 6 detects a failure of the original reference potential supply source, and then automatically performs switching of the reference potential supply sources.

Figure 7A:
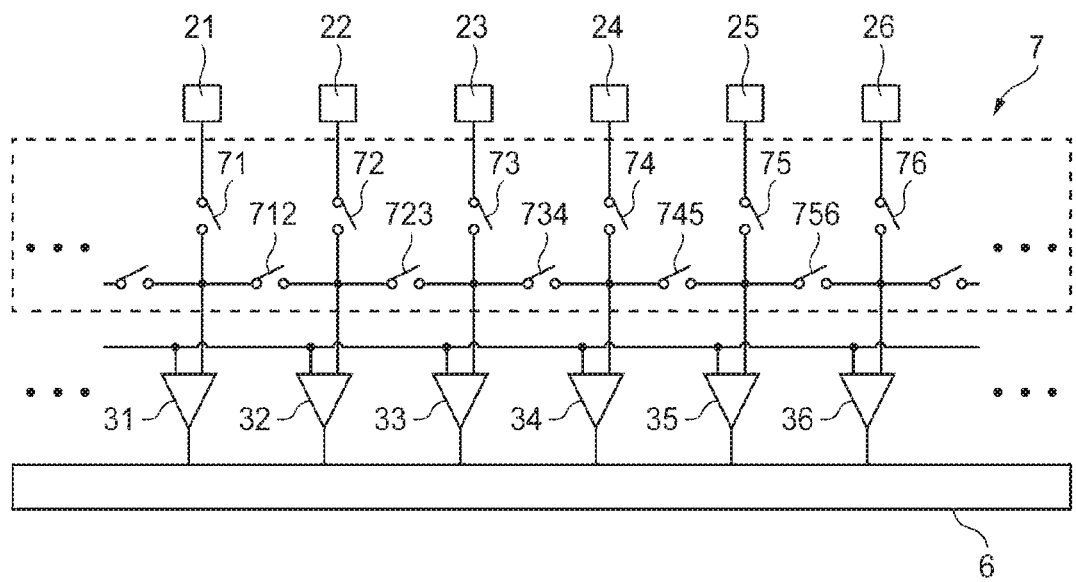
FIGS. 7A and 7B are circuit diagrams showing a further modification of the internal device.

In place of the matrix switch 4 in the above-described embodiment, the internal device 1 may include a ladder-type switch circuit network 7 shown in FIG. 7A. In the example, the electrodes 21 to 26 are shown as a part of the electrode group 2, the amplification elements 31 to 36 are shown as a part of the amplification element group 3, and switch elements 71 to 76 and 712 to 756 are shown as a part of the ladder-type switch circuit network 7.

The input end of the switch element 71 is connected to the electrode 21. The output end of the switch element 71 is connected to the amplification element 31. The switch element 712 can connect the output ends of the adjacent switch elements 71, 72 together. Assuming that n is an arbitrary integer, similarly, the input end of a switch element 7n is connected to an electrode 2n, and the output end of the switch element 7n is connected to an amplification element 3n. Moreover, a switch element 7n(n+1) connects the output end of the switch element 7n to that of a switch element 7(n+1).

Figure 7B:
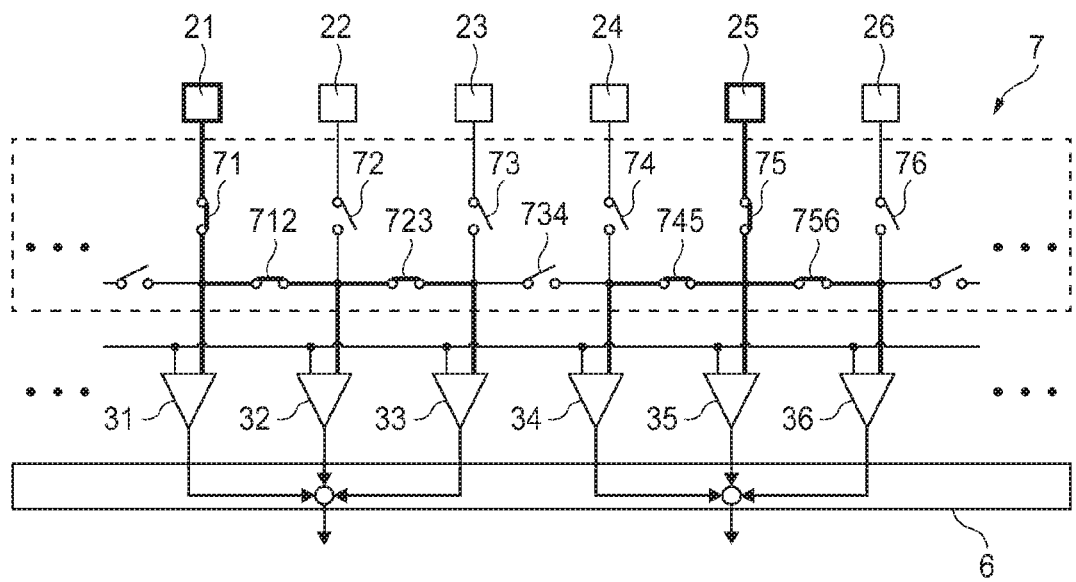

FIG. 7B shows an example of the operation of the thus configured ladder-type switch circuit network 7. When the switch elements 71, 712, 723 are closed, the electroencephalogram signal acquired by the electrode 21 is supplied to the amplification elements 31, 32, 33. When the switch elements 75, 745, 756 are closed, similarly, the electroencephalogram signal acquired by the electrode 25 is supplied to the amplification elements 34, 35, 36.

In the above-described embodiment, the selection of either of the normal operation mode and the noise-reduction operation mode is performed by the controller 6 based on the signal which is received from the external device 200 by the communicator 5. However, the internal device 1 can be configured so as to detect the noise levels of the electroencephalogram signals acquired by the electrode group 2. In this case, based on the detected noise levels, the controller 6 determines whether a significant BMI control can be performed in the normal operation mode or not. If it is determined that a significant BMI control cannot be performed in the normal operation mode, the controller 6 automatically selects the noise-reduction operation mode.

According to an aspect of the presently disclosed subject matter, in the normal operation mode, electroencephalogram signals of the patient are acquired by using as many (the N number of) electrodes as possible. Therefore, also the number of channels for the amplified electroencephalogram signals which are supplied to the external device through the communicator is maximum. Consequently, a rapid BMI control having a high degree of freedom can be performed.

In the case of a patient in whom brain waves diminish with progression of disease, the SN ratio of an acquired electroencephalogram signal is lowered with the progression of the disease. Upon a timing when it is difficult to perform a significant BMI control based on electroencephalogram signals which are acquired in the normal operation mode, the controller can execute the noise-reduction operation mode. At this time, the M number of electrodes are selected from the N electrodes.

In the noise-reduction operation mode, each of the M electroencephalogram signals in which the SN ratio is lowered is supplied to a plurality of amplification elements. As a result, M amplified electroencephalogram signals in which the noise level is lowered as compared with the case of the normal operation mode are obtained. The number of used electrodes, i.e., the channel number is reduced, and therefore it is unavoidable that the degree of freedom of the BMI control is lowered. In brain waves of the patient, however, small changes, which, in the related art, are buried in noise can be distinguished. Even with respect to a patient in whom the intensity of brain waves is reduced with progression of disease, therefore, the possibility of the BMI control can be provided for a long period of time.

What is claimed is:

1. An internal device of a brain-machine interface system, the internal device adapted to be implanted in a living body, the internal device comprising:
   an electrode group which includes a plurality of N electrodes acquiring electroencephalogram signals of the living body, wherein N is 2 or more;
   an amplification element group which includes a plurality of N amplification elements;
   a communicator which is configured to wirelessly communicate with an external device; and
   a controller which is configured to control electrical connections between the plurality of N electrodes of the electrode group and the plurality of N amplification elements of the amplification element group, and which is configured to control the communicator, the controller which is configured to selectively execute one of:
     a normal operation mode in which electroencephalogram signals of the living body that are acquired through the plurality of N electrodes of the electrode group are supplied to the plurality of N amplification elements of the amplification element group in a manner that each electrode of the plurality of N electrodes corresponds to a respective amplification element of the plurality of N amplification elements, and the communicator is caused to wirelessly transmit N amplified electroencephalogram signals that respectively correspond to the plurality of N electrodes; and
     a noise-reduction operation mode in which an electroencephalogram signal of the living body that is acquired through at least one M electrode of the plurality of N electrodes of the electrode group is supplied to the plurality of N amplification elements of the amplification element group in a manner that each electrode of the at least one M electrode corresponds to multiple amplification elements of the plurality of N amplification elements, and the communicator is caused to wirelessly transmit at least one M amplified electroencephalogram signal that respectively corresponds to the at least one M electrode, wherein M is smaller than N.

2. The internal device according to claim 1, wherein in the noise-reduction operation mode the controller is configured to arithmetically average outputs of the multiple amplification elements to acquire the at least one M amplified electroencephalogram signal.

3. The internal device according to claim 1, further comprising:
   a plurality of reference potential supply sources,
   wherein the controller is configured to cause a reference potential supply source of the plurality of reference potential supply sources to be electrically connected to the amplification element group in a switchable manner.

4. The internal device according to claim 1, wherein, based on a signal which is received from the external device by the communicator, the controller is configured to selectively execute one of the normal operation mode and the noise-reduction operation mode.

5. The internal device according to claim 1, wherein, based on noise levels of the acquired electroencephalogram signals, the controller is configured to selectively execute one of the normal operation mode and the noise-reduction operation mode.

6. A method of controlling an internal device of a brain-machine interface system, the internal device adapted to be implanted in a living body, the method comprising:
by a controller of the internal device, selectively executing one of:
a normal operation mode in which electroencephalogram signals of the living body that are acquired through a plurality of N electrodes of an electrode group are supplied to a plurality of N amplification elements of an amplification element group in a manner that each electrode of the plurality of N electrodes corresponds to a respective amplification element of plurality of N amplification elements of the amplification element group, and N amplified electroencephalogram signals that respectively correspond to the plurality of N electrodes are output, wherein N is 2 or more; and
a noise-reduction operation mode in which an electroencephalogram signal of the living body that is acquired through at least one M electrode of the plurality of N electrodes of the electrode group is supplied to the plurality of N amplification elements of the amplification element group in a manner that each electrode of the at least one M electrode corresponds to multiple amplification elements of the plurality of N amplification elements of the amplification element group, and at least one M amplified electroencephalogram signal that respectively corresponds to the at least one M electrode is output, wherein M is smaller than N.

7. The method according to claim 6, wherein in the noise-reduction operation mode outputs of the multiple amplification elements are arithmetically averaged by the controller to acquire the at least one M amplified electroencephalogram signal.

8. The method according to claim 6, further comprising:
by the controller, electrically connecting a reference potential supply source of a plurality of reference potential supply sources to the amplification element group in a switchable manner.

9. The method according to claim 6, wherein the selectively executing of one of the normal operation mode and the noise-reduction operation mode is executed by the controller based on a signal which is wirelessly transmitted from an external device.

10. The method according to claim 6, wherein the selectively executing of one of the normal operation mode and the noise-reduction operation mode is executed by the controller based on noise levels of the acquired electroencephalogram signals.

* * * * *